US012649047B2

(12) United States Patent    (10) Patent No.:    US 12,649,047 B2

Feghali et al.    (45) Date of Patent:    Jun. 9, 2026

---

(54) METHODS AND DEVICES RELATING TO SURGICAL GUIDEWIRE DEVICES

(71) Applicants: Paul Feghali, Boston, MA (US); Anthony Feghali, Syracuse, NY (US)

(72) Inventors: Paul Feghali, Boston, MA (US); Anthony Feghali, Syracuse, NY (US)

( * ) Notice: Subject to any disclaimer, the term of this patent is extended or adjusted under 35 U.S.C. 154(b) by 513 days.

(21) Appl. No.: 18/134,982

(22) Filed: Apr. 14, 2023

(65) Prior Publication Data

US 2024/0180535 A1    Jun. 6, 2024

Related U.S. Application Data

(60) Provisional application No. 63/385,654, filed on Dec. 1, 2022.

(51) Int. Cl.
A61M 25/09 (2006.01)
A61B 17/00 (2006.01)

(52) U.S. Cl.
CPC ....... A61M 25/09041 (2013.01); A61B 17/00 (2013.01); A61B 2017/00469 (2013.01); A61M 2025/09116 (2013.01)

(58) Field of Classification Search
CPC .. A61M 2025/09116; A61M 25/09041; A61M 25/09; A61M 2025/09125; A61B 2017/0042; A61B 17/00; A61B 2017/00469
See application file for complete search history.

(56) References Cited

U.S. PATENT DOCUMENTS

| | | | |
|---|---|---|---|
| 1,151,131 A | 8/1915 | Starliper | |
| 5,137,288 A | 8/1992 | Starkey et al. | |
| 6,190,333 B1 * | 2/2001 | Valencia ......... | A61M 25/09041 |
| | | | 600/585 |
| 7,615,032 B2 | 11/2009 | Whittaker et al. | |
| 9,127,786 B1 * | 9/2015 | Arratia ................ | A61M 25/013 |
| 2002/0026936 A1 * | 3/2002 | Kirn ..................... | A61M 25/013 |
| | | | 128/200.24 |
| 2005/0096566 A1 * | 5/2005 | Arnott ............. | A61M 25/09041 |
| | | | 604/528 |
| 2009/0076417 A1 | 3/2009 | Jones | |
| 2010/0191152 A1 | 7/2010 | Boutillette et al. | |
| 2012/0172845 A1 * | 7/2012 | Kasasbeh ........ | A61M 25/09041 |
| | | | 604/528 |

(Continued)

FOREIGN PATENT DOCUMENTS

| | | | | |
|---|---|---|---|---|
| EP | 2163277 A2 * | 3/2010 | ...... | A61M 25/09041 |
| WO | WO-9004994 A1 * | 5/1990 | ............. | A61B 17/22 |

OTHER PUBLICATIONS

H2O Torq Torque Device; US; Merit Medical.
Round Bore Shaft Hinge Collar; US; Stafford Collars, Couplings & Unique Components.

*Primary Examiner* — Wesley G Harris
(74) *Attorney, Agent, or Firm* — Lisa Foundation Patent Law Clinic; Molly Allen

(57)    ABSTRACT

Systems, methods, and devices relating to guidewire devices that, for example, can be laterally applied to a guidewire and can accommodate a range of guidewire sizes. Guidewire devices may include a hinge, a locking mechanism, or spring-closing mechanisms. The devices may enable medical professionals to safely, accurately, and securely hold, twist, or maneuver guidewires in many types of procedures on humans or other mammals.

22 Claims, 8 Drawing Sheets

(56)                    References Cited

U.S. PATENT DOCUMENTS

| | | |
|---|---|---|
| 2013/0103001 A1 | 4/2013 | BenMaamer et al. |
| 2015/0105650 A1 | 4/2015 | Burkett |
| 2017/0043136 A1* | 2/2017 | Nichols ........... A61M 25/09041 |
| 2019/0070391 A1* | 3/2019 | Dyall .................... A61M 25/01 |
| 2019/0134357 A1* | 5/2019 | Arratia ........... A61M 25/09041 |
| 2020/0276414 A1* | 9/2020 | Bunch ................ A61M 39/1011 |
| 2021/0000493 A1* | 1/2021 | Badadamath .......... A61B 17/22 |

* cited by examiner

FIG. 6A                          FIG. 6B

METHODS AND DEVICES RELATING TO SURGICAL GUIDEWIRE DEVICES

CROSS REFERENCE TO RELATED APPLICATIONS

Priority is claimed to U.S. Provisional Appl. No. 63/385,654 filed on Dec. 1, 2022 which is hereby incorporated by reference herein in its entirety.

FIELD OF THE INVENTIONS

A multitude of minimally invasive medical procedures utilize guidewires and one or more catheters or other medical devices to open blockages, remove clots, sample body tissues, place stents, and perform other procedures. These procedures are performed on humans, horses, dogs, and other mammals. Because guidewires are long, thin wires, physicians often have difficulty maintaining sufficient grip on the guidewire so as to impart torque to their distal end. Therefore, many physicians would benefit from using guidewire torquing devices that attach to the wire to allow for adequate and precise control.

In some instances, guidewire torquing devices may be backloaded over the proximal end of the guidewire and include a sliding locking mechanism or threaded twist locking mechanism that compresses the guidewire to secure it. Torquing devices may involve the user (e.g., a doctor or other medical personnel) sliding the device over the entire proximal length of the guidewire for placement, and two hands to operate. Because of this, physicians may incorporate the assistance of additional medical staff to load torquing devices or control guidewires. In other instances, a guidewire torquing device may have side loading capabilities configured to grasp guidewires in a channel to be usable with one-handed operation. In some instances, side loading devices do not entirely enclose the wire when engaged, and may involve internal or external devices for self-tensioning to allow physicians to maintain control of the wire.

In some instances, guidewire torquing devices may be configured to accommodate one size of guidewire. Without a universal device, physicians and medical staff may be asked to determine ahead of time how many torquing devices may be needed for a procedure in a particular size, and that assessment can present challenges. If these size determinations are incorrect, it may result in a situation where staff enter or leave a sterile area, or worse, attempt to carry out the procedure without the proper size of torquing device needed. In some instances, because guidewire devices might be passed along the length of the distal end of the wire, there is a heightened risk of dislodging the wire and losing endovascular access across a target vessel, increasing procedure time and potential risk factors.

A side loading guidewire torquing device that, in some instances, is configured or configurable to enclose a guidewire when engaged, does not require additional machinery for maintaining torque, and can accommodate a range of wire gauges and diameters is useful to enhance medical procedures and outcomes, aids in the fluidity of medical procedures, and reduces complications.

INTRODUCTION

So as to reduce the complexity and length of this specification, the materials identified the following paragraphs in this section are herein expressly incorporated by reference in their entirety. The incorporated material is believed to be non-essential in accordance with 37 CFR 1.57 because it is referred to for purposes of providing general support, background, or information relating to the inventions. However, if any such material is deemed essential under Rule 1.57, any such necessary text will be expressly added herein pursuant to applicable rules.

U.S. Pat. App. Pub. No. 2013/0103001 may generally concern, among other things, guidewires and screw threaded guidewire devices.

U.S. Pat. No. 5,137,288 may generally concern, among other things, guidewires and screw threaded guidewire devices.

US. Pat. App. Pub. No. 2010/0191152 may generally concern, among other things, clamshell devices for applying torque to guidewires.

U.S. Pat. App. Pub. No. 2009/0076417 may generally concern, among other things, self-tensioning apparatuses for guidewires.

U.S. Pat. App. Pub. No. 2015/0105650 may generally concern, among other things, generally cylindrically shaped guidewire devices.

U.S. Pat. No. 7,615,032 may generally concern, among other things, guidewire devices have side-access channels and collets.

Unless specifically noted, words and phrases in this specification and the claims are to be given their relevant plain and ordinary English meaning. Thus, except where this specification uses the exact phrase "[word or phrase] is hereby defined to mean [definition]," the inventor expressly elects, as lexicographer, to use the plain and ordinary meaning of words in the specification and claims rather than special definitions. Absent such specific statement to apply a special definition, the plain and ordinary meaning applies to the terms used in the specification and claims.

The inventor is also aware of the normal precepts of English grammar. Thus, if a noun, term, or phrase is intended to be characterized, specified, limited, broadened, modified or narrowed in some way, then such noun, term, or phrase will expressly include any desired or intended adjectives, descriptive terms, or other modifiers in accordance with the normal precepts of English grammar. Absent the use of such adjectives, descriptive terms, or modifiers in the claim language, it is intended that such nouns, terms, or phrases be given their ordinary and customary meaning as set forth above.

Further, the inventor is aware of the availability and limits of functional claiming under 35 U.S.C. § 112(f). As used herein or in the claims, the words "function," "means" or "step" do not indicate an intent to invoke the special provisions 35 U.S.C. § 112(f) to define the inventions. To the contrary, if the provisions of 35 U.S.C. § 112(f) are sought to be invoked to define the inventions, the claims will specifically and expressly recite the exact phrase "means for" and will also expressly recite the word "function" followed by a description of the function (i.e., will state: "means for performing the function of [insert function]"), without also reciting in such phrases any structure, material or act in support of the function. Thus, even if a claim recites a "means for performing the function of . . ." if a claim also recites any supporting structure, material or acts then it is the clear intention of the inventor not to invoke the provisions of 35 U.S.C. § 112(f). If the provisions of 35 U.S.C. § 112(f) are invoked to define the claimed inventions (using the technique defined above), it is intended that the inventions not be limited only to the specific structure, material or acts that are described in any specific embodiment, but in addition, include any equivalent structures, materials, or acts that perform the claimed function, or any structures, materials, or acts described in any alternative situations or forms of the inventions, or that are within the appropriate limits of claim scope and construction and that are reasonably described and reasonably enabled by this specification.

The inventions described in this specification and recited in the claims are not directed to laws of nature, natural phenomena, or abstract ideas, but instead, are directed to one or more of the expressly permitted statutory categories of inventions, i.e., processes, machines, manufactures, or compositions of matter. Nor are the inventions claimed herein directed to any prohibited examples of abstract ideas such as fundamental economic practices, methods of organizing human activity, an idea itself, or any mathematical relationships/formulas. The claimed inventions are directed to significantly more than any abstract idea by itself and include specifically claimed inventive concepts so as to not preempt any fundamental building blocks of human ingenuity.

Numerous possible or potential aspects, objects, modifications, features, uses, or advantages of various inventions described herein will be apparent to those of ordinary skill in the art from this specification, drawings, and claims. However, without characterizing or limiting the scope of the various inventions as they are claimed, some of the possible or potential aspects, objects, features, uses, or advantages of various inventions are summarized below. None of the following possible or potential aspects, objects, features, uses, or advantages are a disavowal, disclaimer, characterization, or interpretation of any aspects of any of the claims. These possible or potential aspects, objects, features, uses, or advantages might apply to any or none of the claimed inventions.

It may be an object, goal or advantage of some of the inventions to enable a user to apply torque to a guidewire device during surgical procedures involving opening blockages, removing clots, sampling body tissues, or performing other procedures.

It may be an object, goal or advantage of some of the inventions to enable users to insert guidewires laterally.

It may be an object, goal or advantage of some of the inventions to accommodate a range of guidewire sizes or gauges. Instead, some examples of guidewire torquing devices described herein are able to accommodate one size of guidewire, while others enable one device to accommodate many or all sizes of guidewires in use during a procedure thereby streamlining procedures.

It may be an object, goal or advantage of some of the inventions to make medical practices safer, more effective, and beneficial to patients.

It may be an object, goal or advantage of some of the inventions to save time in making medical decisions regarding the sizes or shapes of guidewires and related holding or torquing devices.

It may be an object, goal or advantage of some of the inventions to leverage innovative materials such as plastics, composites, and other compound and innovative fabrication techniques to construct the inventive guidewire devices.

It may be an object, goal or advantage of some of the inventions to enable various unique locking and unlocking hardware or techniques for opening or closing guidewire devices onto various guidewires.

BRIEF DESCRIPTION OF THE DRAWINGS

Additional understanding of the inventions may be derived by referring to the description when considered in connection with the figures. In the figures, like reference numbers refer to like elements or acts. While the figures provide several examples of aspects, elements, modifications, or components that may or may not be variously involved with the systems, methods, and devices described herein, the figures are not provided to define, limit, or affect the scope of the inventions claimed or described herein. Rather, the words of the claims are intended to define and control the scope of the inventions claimed herein.

FIGS. 6A, 6B, and 6C generally represent top and bottom perspective views of an example guidewire device.

Figure 1:
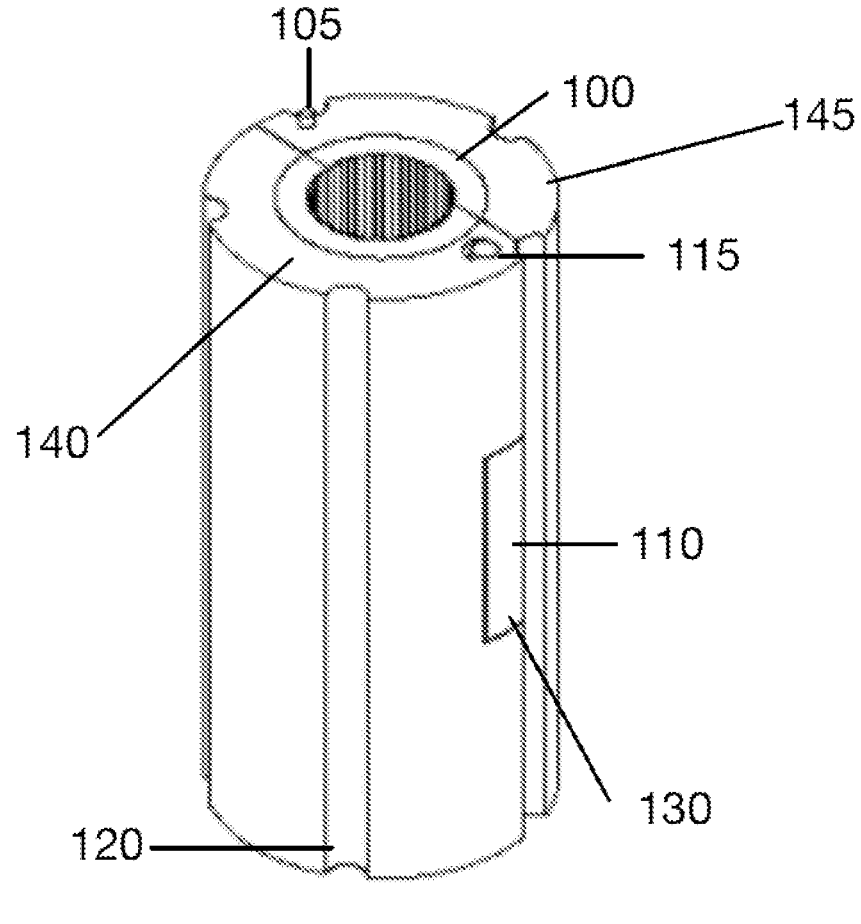
FIG. 1 generally represents a three-dimensional view of an example guidewire device.

Elements and acts in the figures are illustrated for simplicity, may not be to scale, and have not been rendered according to any particular embodiment or example and do not depict any essential or required claim limitations. Instead, the claims rather than the drawings define the metes and bounds of the various inventions.

DETAILED DESCRIPTION

The inventions are explained in additional detail below.

In one example, the guidewire device may comprise a first member and a second member each having a body, a hinge end, a locking face, a first side face, and a second side face. This example may further comprise a hinge mechanism. The hinge end of the first member may further comprise a first ear and a second ear. The first ear and second ear may comprise an outer face, an inner face, and a front face. Additionally, the body of the first member may comprise a channel face that is in between the inner face of the first ear and the inner face of the second ear. The inner face of the first ear, the inner face of the second ear, and the channel face may form a channel. The hinge end of the second member may comprise a hinge member that may have a first side face, a second side face, and an outer face. The first side face of the hinge member may be configured to be coupled with the inner face of the first ear, the second side face of the hinge member may be configured to be coupled with the inner face of the second ear, and the outer face of the hinge member may be configured to be coupled with the channel face of the body. The inner face of the first ear may comprise an opening extending into the body of the first member on an axis that is parallel to a guidewire when the device is in use. The inner face of the second ear may comprise an opening extending into the body of the first member on an axis parallel to a guidewire. The hinge member may comprise a cavity that extends from the first side face through to the second side face at an axis parallel to a guidewire. The first member and the second member may be hingedly coupled by a rod and hinge spring that may run through the openings within the first ear, hinge member, and second ear.

In some cases, a guidewire device may include a locking mechanism. This locking mechanism may include a receiving end and a notched end. The receiving end may be positioned on the locking face of the first member and may comprise a pin and spring that may be oriented parallel to a guidewire when the device is in use. The spring may be wrapped around the pin so as to form a tensioned pin and spring system. The tensioned pin and spring system may be configured to extend through the body and into an opening on the locking face of the first member. The tensioned pin and spring system may be further configured to securely catch the notched end that may be found on the locking face of the second member. The notched end may be configured to have multiple locking points so that the device can accommodate a range of wire diameters. In some cases, guidewire devices may employ an alternative locking mechanism that may have one locking point.

A first member may comprise a first side face and second side face. The first side face of the first member may further comprise a button, wherein the button may comprise a rod that may extend through the body on an axis that is parallel to the tensioned pin and spring system of the first member and may be coupled with the tensioned pin and spring system. The button may further comprise a first end and a second end, wherein the first end may protrude from the first side face of the first member and the second end may be configured to couple to the tensioned pin and spring system. The button may be configured such that when the first end is compressed, the second end may thereby compress the tensioned pin and spring system to release the notched end.

In some cases, the device may be configured to have an open configuration and a closed configuration. The device may be further configured to be applied laterally to a guidewire when in the open configuration. The device may be further configured to be securely fixed onto the guidewire and enable a user to apply torque when the device is in the closed configuration and the notched end is coupled to the tensioned pin and spring system.

In some cases, guidewire devices may include a first member and a second member each having a first end and a second end. The first member and the second member may be combined using a hinge system. In some examples, guidewire devices may include a locking mechanism.

For example, the first member and the second member may comprise an inner surface and an outer surface. An inner surface of the first member and the inner surface of the second member may further comprise a padding material of a specified thickness. An outer surface of the first member and second member may be textured so as to allow for better handling of the device.

In another example, a first body 140 and a second body 145 are used. The first body 140 may comprise a first padded, substantially half-cylindrical groove 100. (Referring to FIG. 1). The first groove 100 may extend laterally into the first body 140. Additionally, the second body 145 may comprise a second padded, substantially half-cylindrical groove 100. The second half-cylindrical groove 100 may extend laterally into the second body 145.

In some cases, guidewires may be laid in the first half-cylindrical groove 100 of the first body 140. The second body 145 may be rotated into a closed position such that the first padded half-cylindrical groove 100 and the second padded half-cylindrical groove 100 form a general circle around an outer surface of the guidewire 500, so as to securely hold the guidewire 500 within the inventions. (Referring to FIGS. 1 and 5). The first body 140 and second body 145 may be coupled to one another latitudinally around a rotational axis. Additionally, the first body 140 and the second body 145 may be configured to come into contact with one another using a friction coupling when rotated into a closed position so as to lock together and remain in place relative to the guidewire 500 when in use. The inventions may be configured to facilitate the insertion of the distal end of a guidewire 500 into the human body for surgical procedures.

Referring to FIG. 1, an example guidewire device is shown that includes, for example, a first body 140 and a second body 145. There may be a half-cylindrical groove 100 present on the first body 140 and the second body 145 that is configured to receive a guidewire 500. The half-cylindrical groove may have a layer of padding 205 that may be used to keep the guidewire in place while the inventions are in use. (Referring to FIG. 2). The padding 205 may be selected from various materials, including polyester, polyether, polystyrene, polyurethane, or vinyl, among others. The first body and second body may be made of a material such as polyethylene, polyethylene terephthalate, polyvinyl chloride, polypropylene, polystyrene, or others.

In some instances, the first body 140 may have a textured, grooved, or otherwise abrasive material coupled to the outer surface 120. (Referring to FIG. 1). The textured or grooved outer surface 120 improves grip and torquing ability. The inventions may be formed using plastic extrusion, injection molding, or other techniques. The inventions may have a Shore A Hardness scale factor between 20A-90A, and a Shore D Hardness scale factor between 40D-90D.

Figure 2:
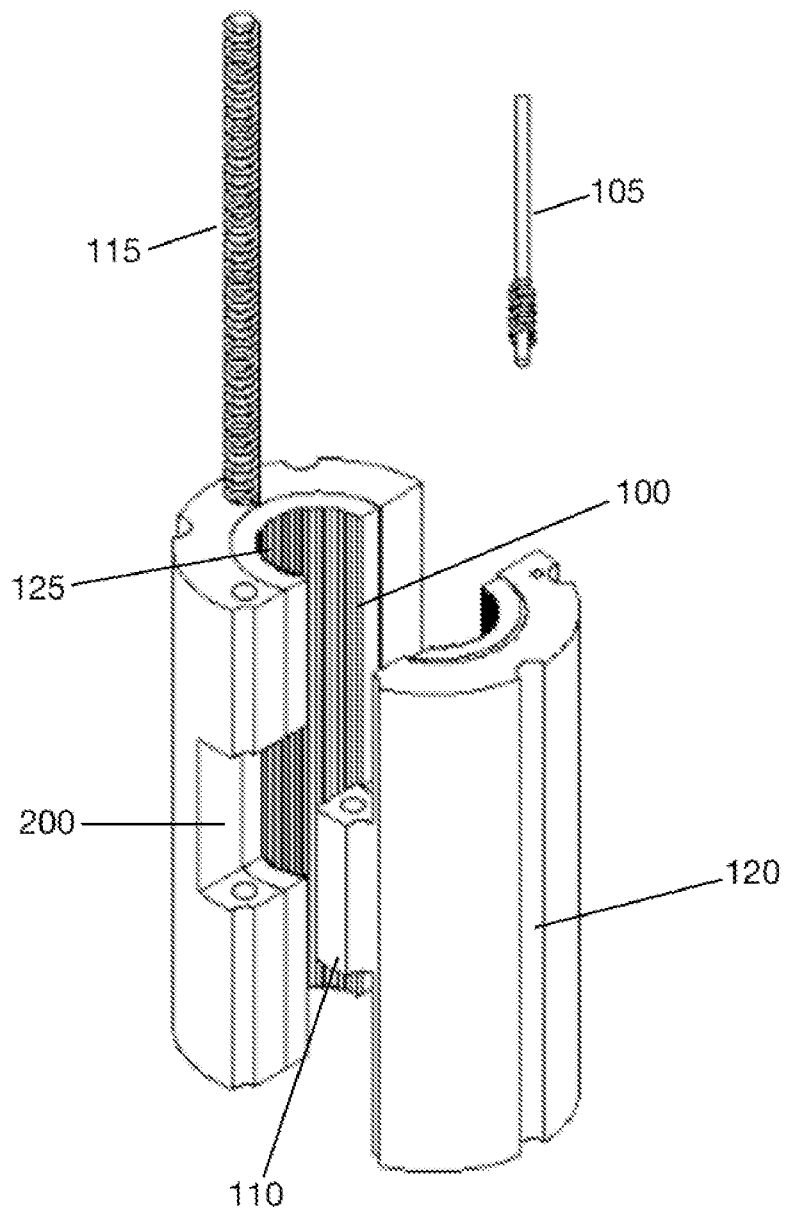
FIG. 2 generally represents an exploded three-dimensional view of an example guidewire device.

Referring to FIG. 2, an example guidewire device is shown that includes, for example, a hinge system 110. The hinge system may couple the first body 140 to the second body 145. The hinge system 110 may be selected from multiple styles of hinges, including a pin hinge mechanism, squeeze release mechanism, pinch release mechanism, a rod and spring mechanism, or others. A male hinge end 135 can be placed on a first body 140 that is configured to fit into a female hinge end 200 present on a second body 145. An internal channel may run longitudinally through the first body 140 and second body 145 that allows a rod and spring to be inserted to form a hinge mechanism 110 that keeps the first body 140 and second body 145 together while the inventions are in use.

Figure 3:
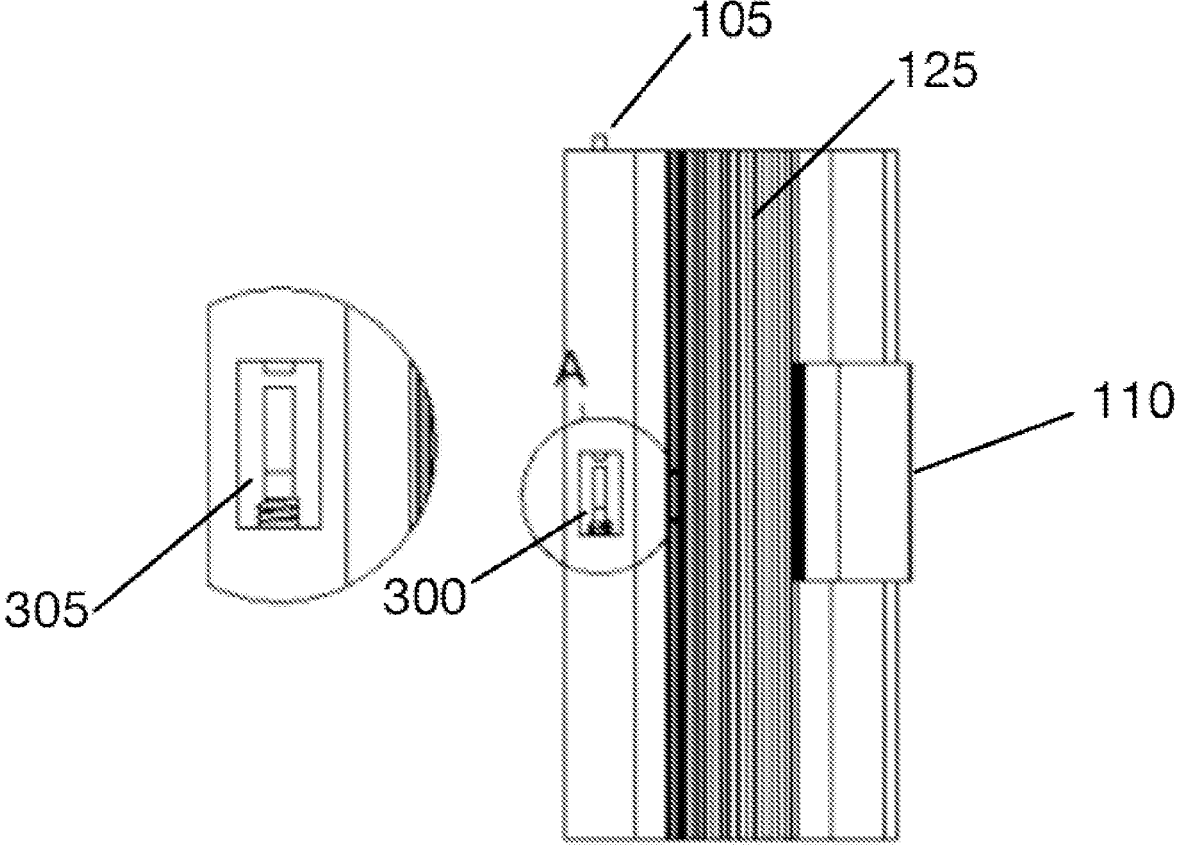
FIG. 3 generally represents a cross sectional view of an example guidewire device.
Figure 4:
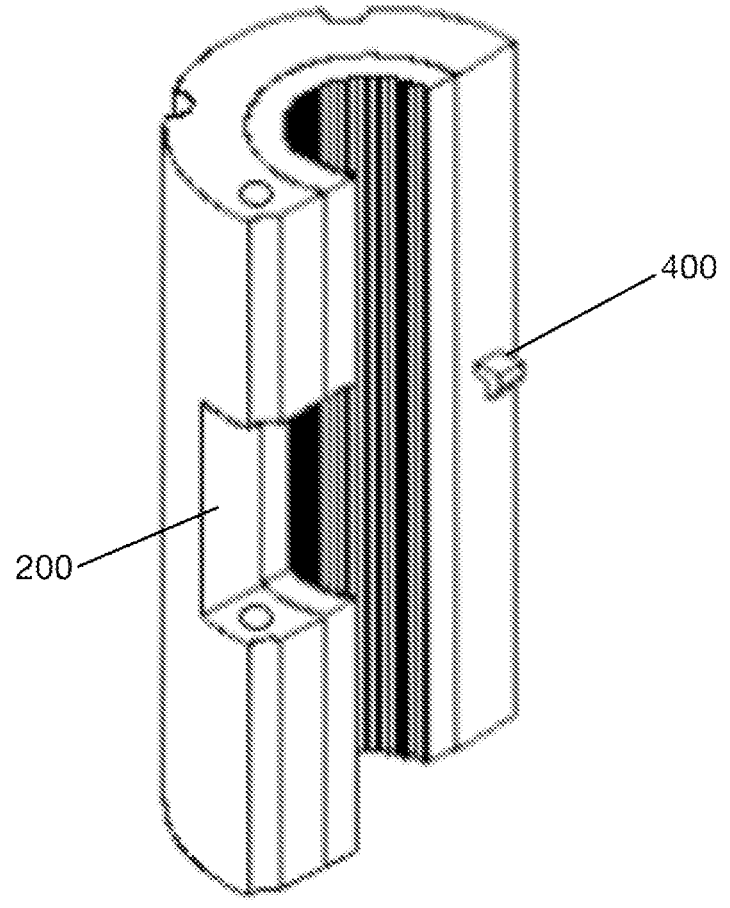
FIG. 4 generally represents a perspective view of half of an example guidewire device.

Referring to FIGS. 3 and 4, example guidewire devices are shown that include, for example, a friction lock with an L-shaped or hook-shaped protrusion 400 and one or more attachment points 300. Alternatively, a coupling with a male side and a female side could be used. The attachment points 300 may contain an internal rod and spring mechanism 305. The male lock end 400 may be configured to fit into the attachment points 300 to lock in place while the inventions are in use. In some instances, the internal rod and spring mechanism 305 may contain a first rod 105 that extends through the first body 140 or second body 145 of the inventions, and terminates past the end of the first body 140 or second body 145 to form a button 105 that can be compressed to release the male lock end 400. When a user compresses the button, the internal rod may be compressed, forming a space that allows the protrusion to be released. The locking mechanism may be configured so that it only requires one hand to open and close the inventions. The outer diameter of the first body may be between 0.25"-4".

Figure 5:
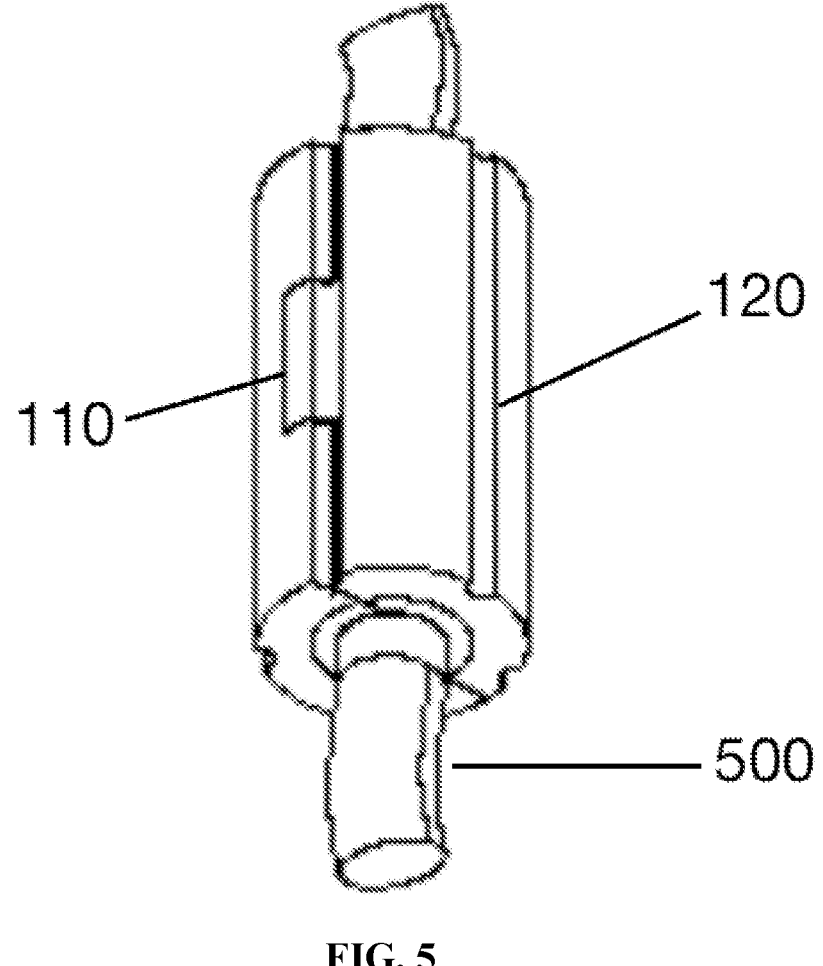
FIG. 5 generally represents a three-dimensional view of an example guidewire device engaged with a guidewire.

Referring to FIG. 5, a guidewire device is configured to hold a guidewire 500 in place.

Figure 6C:
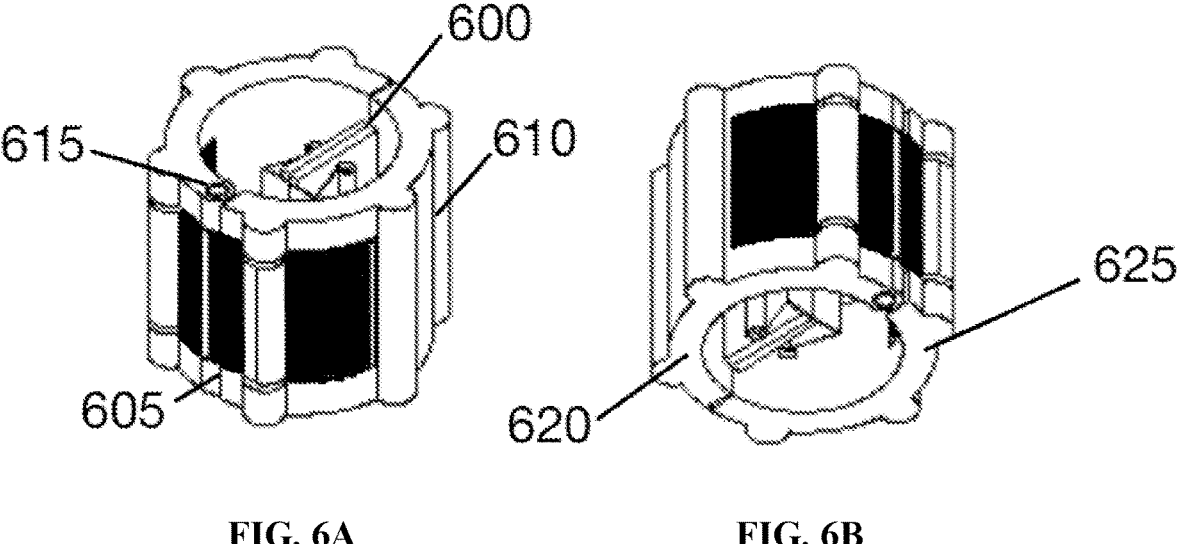
Figure 6C:
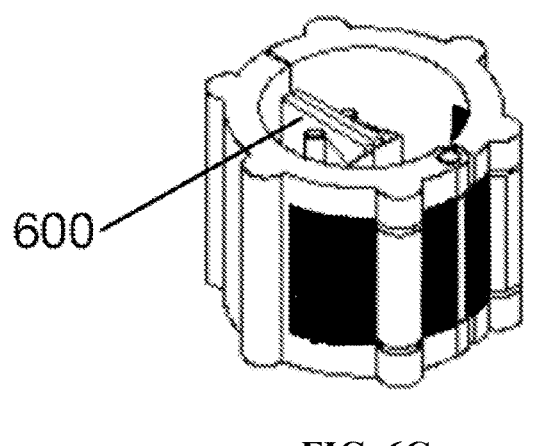
Figure 7A:
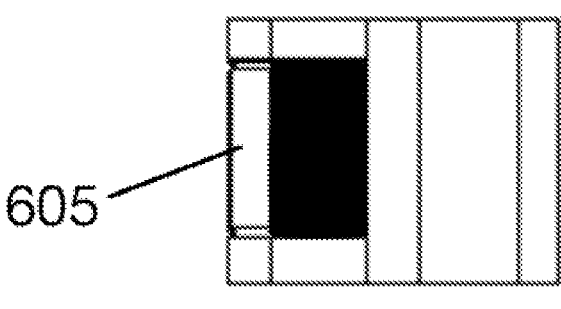
FIGS. 7A, 7B, and 7C generally represent elevation views of an example guidewire device.
Figure 7B:
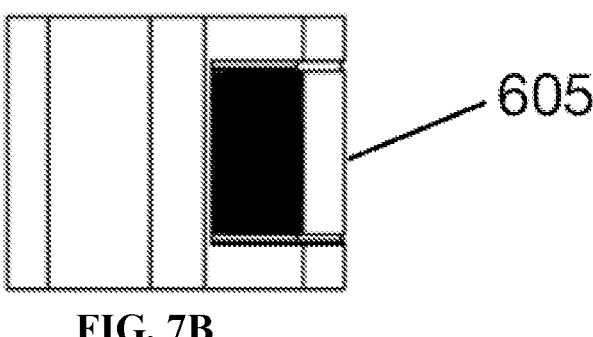
Figure 7C:
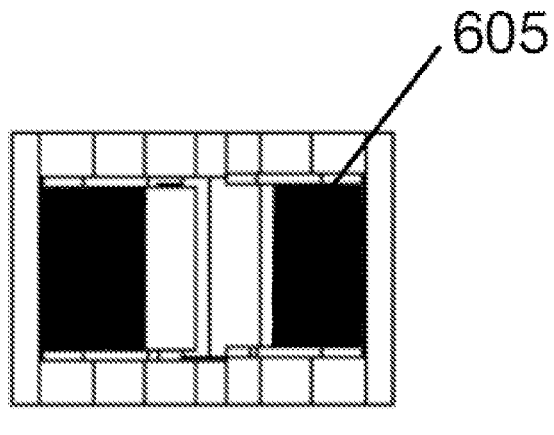

Referring to FIGS. 6A, 6B, and 6C, an example guidewire device is shown that includes, for example, a hinge mechanism 605. The hinge mechanism may comprise a spring and pin system 615 that may couple the first body 620 to the second body 625. The hinge mechanism may be selected from various locking mechanisms, including a squeeze release mechanism, a lock and pin mechanism, a pinch release mechanism, or others. The hinge mechanism 605 may open and close the inventions to allow for the insertion of a guidewire 500. The hinge mechanism 605 may be configured so that it only requires one hand to open and close the inventions. A user may grab the inventions, open the hinge with their dominant hand, and use their wrist to turn the inventions into a position to accept the guidewire. Alternatively, a user may grab the inventions, open the hinge with their non-dominant hand, and use their wrist to turn the inventions into position to accept the guidewire. The first body may have gaps where a user can insert their fingers to aid in leverage when opening the hinge.

Figure 8A:
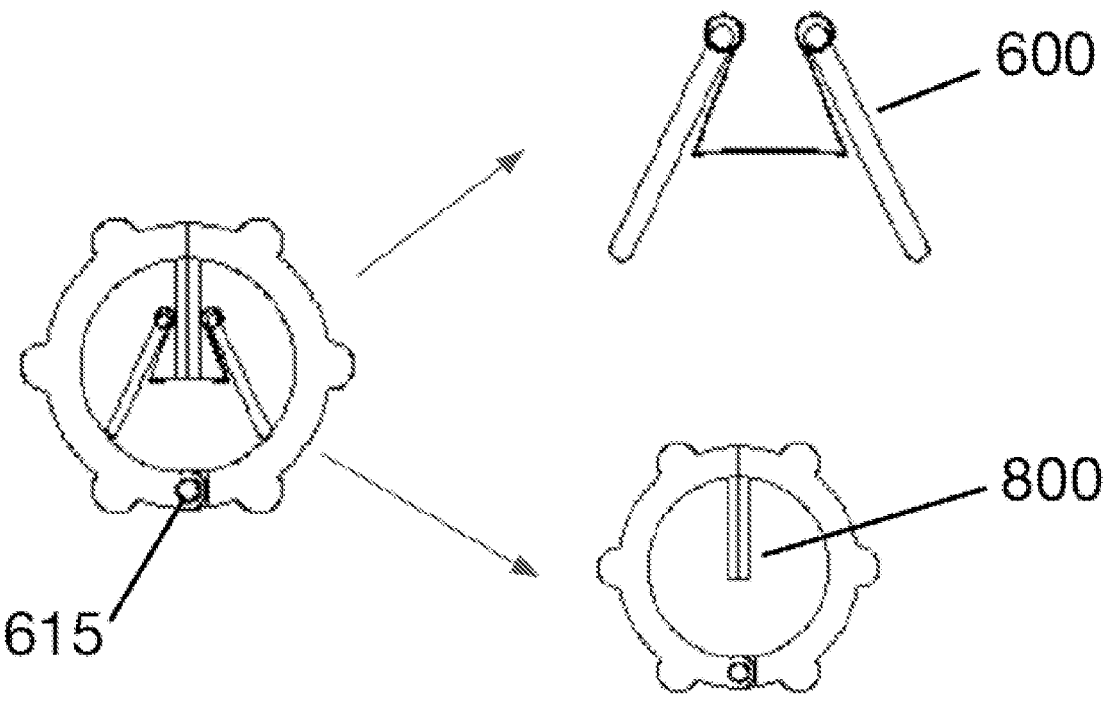
FIG. 8A generally represents a top view of various components of an example guidewire device.

Referring to FIG. 8A, an example guidewire device is shown that includes, for example, a clip mechanism 600. The clip may have a set of wings coupled to the inner surface of the first and second body. There may be a set of plates 800 within the clip mechanism designed to hold the guidewire 500 in place while the inventions are in use. There may be a padding material coupled to the plates 800 selected from various materials, including polyester, polyether, polystyrene, polyurethane, or vinyl, among others. The plates 800 may be flat or contoured. In some instances, the plates 800 may be textured, grooved, or have an abrasive material coated thereon. Additionally, the plates 800 may have padding. When the hinge is opened, the clip may be compressed and allow the plates to separate, allowing a user to grip a guidewire. When the handles of the hinge are released, the clip may be released and compress the plates, securing the guidewire in place.

Figure 8B:
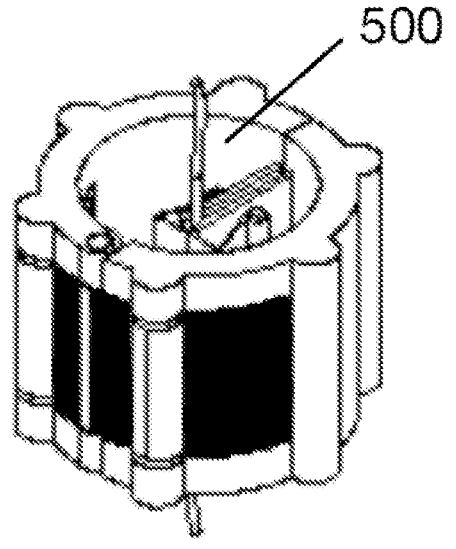
FIG. 8B generally represents a perspective view of an example guidewire device engaged with a guidewire.

Referring to FIG. 8B, a guidewire device is configured to hold a guidewire 500 in place.

In the foregoing description, numerous examples and details are set forth to provide a clear understanding of various aspects of various inventions together with a written description of the claimed subject matter and to enable a person of ordinary skill in this field to make and use the same. It will also be understood, by those skilled in the relevant arts, that the present inventions may be practiced without, or with various alternatives, modifications, and/or equivalents of various of these details. In other instances, structures and devices are omitted or shown or discussed more generally in order to avoid obscuring or unduly limiting the inventions. In many cases, a description of operations is sufficient to enable one to implement the various forms of the inventions. It should be noted that there are many different, alternative, or equivalent configurations, devices, and technologies to which the disclosed inventions may be applied. The full scope of the inventions is not limited to the examples that are described herein.

We claim:

1. A method of attaching a guidewire device to a guidewire comprising:

laying the guidewire in a first groove of a first body, the first body having a substantially half-cylindrical shape, and the first groove being padded;

rotating a second body, having a substantially half-cylindrical shape, around a rotational axis into a closed position such that a first edge of the first body directly contacts a second edge of the second body, and the first groove and a second groove of the second body form a general circle around an outer surface of the guidewire, wherein the second groove is padded;

wherein the first groove and the second groove cooperate to contact an outer surface of the guidewire and securely hold the guidewire within the guidewire device;

wherein, the first body and second body are hingedly coupled to one another by a locking mechanism comprising a notched end on the first edge and a receiving end on the second edge;

wherein the receiving end includes a tensioned pin and spring system that engages to fix the notched end into the receiving end when the device is in the closed position, the tensioned pin and spring system being oriented parallel to the guidewire; and wherein the first body and second body, when rotated into the closed position, form a substantially circular body and are fixed while the device is in use by the engagement of the locking mechanism to enable a user to apply torque to the guidewire.

2. The method of claim 1, wherein the first body and the second body cooperate to form a substantially cylindrical exterior shape.

3. The method of claim 1, further comprising inserting a distal end of the guidewire into a human body while holding the guidewire device.

4. The method of claim 1, wherein the first body and the second body are fixed by way of a friction coupling.

5. The method of claim 1, wherein the first body and the second body lock together.

6. The method of claim 1, wherein, as a result of the guidewire device having capability of being opened, repositioned, and closed with a single hand of the user, the second body is capable of being rotated into the closed configuration by the single hand.

7. The method of claim 1, wherein the guidewire device is configured to be selectively opened, repositioned relative to the guidewire, and closed using only a single hand of the user, and wherein, as a result of operability via said single hand, the second body is configured to be rotationally actuated by the single hand of the user relative to the first body into the closed configuration while the first body is simultaneously stabilized by the same hand.

8. A guidewire device adapted to be secured to and released from a guidewire, the device comprising:

a first body having a substantially half-cylindrical shape and defining a first groove extending laterally therein, the first groove being padded to form a first padded half-cylindrical groove, wherein the first groove is on an inner surface of the first body and has a substantially half-cylindrical shape extending laterally in the first body;

a second body having a substantially half-cylindrical shape and defining a second groove extending laterally therein, the second groove being padded to form a second padded half-cylindrical groove;

a friction coupling that mechanically couples the first body to the second body, the friction coupling including:

a protrusion located on a first edge of the first body facing a complementary second edge of the second body;

a receiving end on the second edge comprising a tensioned pin and spring system, the receiving end being positioned across from the protrusion and shaped to receive the protrusion into a locking arrangement;

a button located on a first side face of the first body, comprising a rod that extends through the first body on an axis that is parallel to the tensioned pin and spring system of the receiving end and may be coupled with the tensioned pin and spring system such that when the button is compressed, the tensioned pin and spring system releases the protrusion from the receiving end;

wherein the first body is coupled, by a hinge, to the second body latitudinally around a rotational axis that is parallel to the guidewire's axis, such that the first body and the second body are configured to rotate around the rotational axis with respect to each other from an open configuration to a closed configuration, wherein the first body and the second body are configured to be brought and held into contact with one another by the friction coupling when rotated into the closed configuration so as to lock together and remain in place relative to the guidewire when in the closed configuration; and wherein the first body and second body, when rotated into the closed configuration, are configured to come into contact with one another and be fixed together relative to the guidewire via locking engagement of the protrusion with the receiving end and the tensioned pin and spring system, wherein, when locked together in the closed configuration, the first padded half-cylindrical groove and the second padded half-cylindrical groove form a general circle around an outer surface of the guidewire, so as to contact the guidewire and securely hold the guidewire within the guidewire device and enable a user to apply torque when the device is in the closed configuration and the notched end is coupled to the tensioned pin and spring system.

9. The device of claim 8, wherein the first body and second body cooperate to form a substantially cylindrical exterior shape.

10. The device of claim 8, wherein the first body and the second body are fixed by way of the friction coupling.

11. The device of claim 8, wherein the first body and the second body lock together.

12. The device of claim 8, wherein the first groove is on an inner surface of the first body.

13. The device of claim 12, wherein the padding of the first groove is comprised of silicone, polyester, polyether, polystyrene, polyurethane, or vinyl, among others.

14. The device of claim 8, wherein the first body and second body have an outer surface that is textured, grooved, or abrasive.

15. The device of claim 8, wherein the each of the first groove and the second groove have a substantially semi-circular shape.

16. A guidewire device comprising:

a substantially circular body having a first body hingedly coupled to a second body, wherein in a closed position a first surface of the first body directly contacts a first surface of the second body and in an open position the first surface of the first body is spaced apart from the first surface of the second body;

wherein a first plate is fixed to the first body and wherein a second plate is fixed to the second body; and a clip comprised of a set of wings integrally coupled together by a bridge portion to form a substantially triangularly-shaped spring clamp that biases end portions of the set of wings towards each other into a closed position;

wherein the set of wings is coupled to an inner surface of the first body and the second body having first ends that engage the first and second plates, respectively, and a set of jaws held together by the substantially triangularly-shaped spring clamp;

wherein the clip is disposed, in entirety, radially within the substantially circular body, wherein the set of jaws of the clip are configured to compress the first and second plates around a guidewire and thereby frictionally secure the guidewire device in place on the guidewire as a result of compressive force of the substantially triangularly-shaped spring clamp;

wherein the guidewire device is configured to hold the guidewire in position between either:

(1) an inner surface of the first plate at a distal end of the first plate abutting the bridge portion of the clip, an inner surface of the second plate at a distal end of the second plate, and the bridge portion of the substantially triangularly-shaped spring clamp of the clip; or (2) opposing inner surfaces of the first plate and the second plate.

17. The device of claim 16, wherein the first body is made of a material such as polyethylene, polyethylene terephthalate, polyvinyl chloride, polypropylene, polystyrene, or others.

18. The device of claim 16, wherein the first body and second body are fixed by way of a friction coupling.

19. The device of claim 18, wherein the first plate and the second plate are configured to cooperate to hold the guidewire securely in place when the first body and second body lock together.

20. The device of claim 16, wherein the first body has an outer surface that is textured, grooved, or abrasive.

21. The device of claim 16, wherein an outer surface of the first body comprises an opening configured to provide access to a hinge mechanism.

22. The device of claim 16 that is configured for operation with a single hand of a user in that:

when a hinge is actuated by the single hand, the clip is compressed, thereby separating the first and second plates to permit lateral insertion of the guidewire between the first and second plates, and when the hinge is released by the single hand of the user, the clip biases the first and second plates toward one another into a compressed configuration, thereby securing the guidewire between the first and second plates.

* * * * *